United States Patent [19]

Bowman

[11] Patent Number: 5,329,934
[45] Date of Patent: Jul. 19, 1994

[54] MEDICAL PATIENT RESTRAINT DEVICE
[76] Inventor: Karolen C. Bowman, P.O. Box 2084, North Wilkesboro, N.C. 28659
[21] Appl. No.: 987,663
[22] Filed: Dec. 9, 1992
[51] Int. Cl.[5] .......... A61G 15/00; A61G 7/00; A61F 5/37; A47C 27/14
[52] U.S. Cl. ............... 128/845; 128/870; 128/876; 5/655; 5/922; 5/632; 5/603
[58] Field of Search .......... 128/845, 846, 869, 870, 128/871–875, 876, 883; 5/655, 424, 922, 632, 603, 601

[56] References Cited

U.S. PATENT DOCUMENTS

| | | | |
|---|---|---|---|
| Re. 24,377 | 10/1957 | Creelman | 5/603 |
| 1,980,848 | 11/1934 | Cass | 250/34 |
| 2,777,138 | 1/1957 | Gallagher | 5/655 |
| 3,034,502 | 5/1962 | Lund | 128/870 |
| 3,215,334 | 11/1965 | Tayman | 250/54 |
| 3,358,141 | 12/1967 | Hoffmann et al. | 128/870 X |
| 3,369,548 | 2/1968 | Moore et al. | 128/869 |
| 3,526,222 | 9/1970 | Dreibelbis | 128/134 |
| 3,650,523 | 3/1972 | Darby, Jr. | 269/328 |
| 3,828,377 | 8/1974 | Eary, Sr. | 5/922 X |
| 4,027,869 | 6/1977 | Ruiz | 269/328 |
| 4,030,719 | 6/1977 | Gabrele et al. | 5/603 X |
| 4,108,168 | 8/1979 | Craig | 128/80 |
| 4,205,669 | 6/1980 | Hamann | 128/870 |
| 4,383,713 | 5/1983 | Roston | 5/922 X |
| 4,693,212 | 9/1987 | Black | 119/103 |
| 4,757,811 | 7/1988 | Clark | 128/134 |
| 4,840,362 | 6/1989 | Bremer et al. | 5/922 X |
| 4,854,305 | 8/1989 | Bremer | 128/75 |
| 4,911,106 | 3/1990 | Goodwin | 119/103 |
| 5,027,833 | 7/1991 | Calkin | 128/870 |
| 5,056,533 | 10/1991 | Solano | 128/876 X |
| 5,076,288 | 12/1991 | Millard et al. | 128/869 |
| 5,127,422 | 7/1992 | Colón | 128/870 X |

*Primary Examiner*—Robert A. Hafer
*Assistant Examiner*—Brian E. Hanlon
*Attorney, Agent, or Firm*—Bell, Seltzer, Park & Gibson

[57] ABSTRACT

A medical patient restraint device is provided for additional comfort while restraining patients during surgical procedures such as the circumcision of infants. The patient restraint device has a generally planar support member which is sized to receive and support a patient in a lying position thereon. The support member defines opposite side edges. A pair of support straps are fixed to the support member and extend along respective side edge portions in a generally parallel relationship. The pair of support straps are laterally spaced apart a distance sufficient to receive the patient therebetween with the support straps being parallel to and adjacent the sides of the patient. Individual restraining straps are provided for releasable connection to respective ones of the patient's arms and legs. Mating fasteners are fixed to the pair of support straps and the individual restraining straps such that each of the restraining straps may be releasably attached to one of the pair of support straps so as to permit the individual straps to retain the patient in a spread-eagle position on the support member and without having the individual restraining straps extending across the torso of the patient.

14 Claims, 2 Drawing Sheets

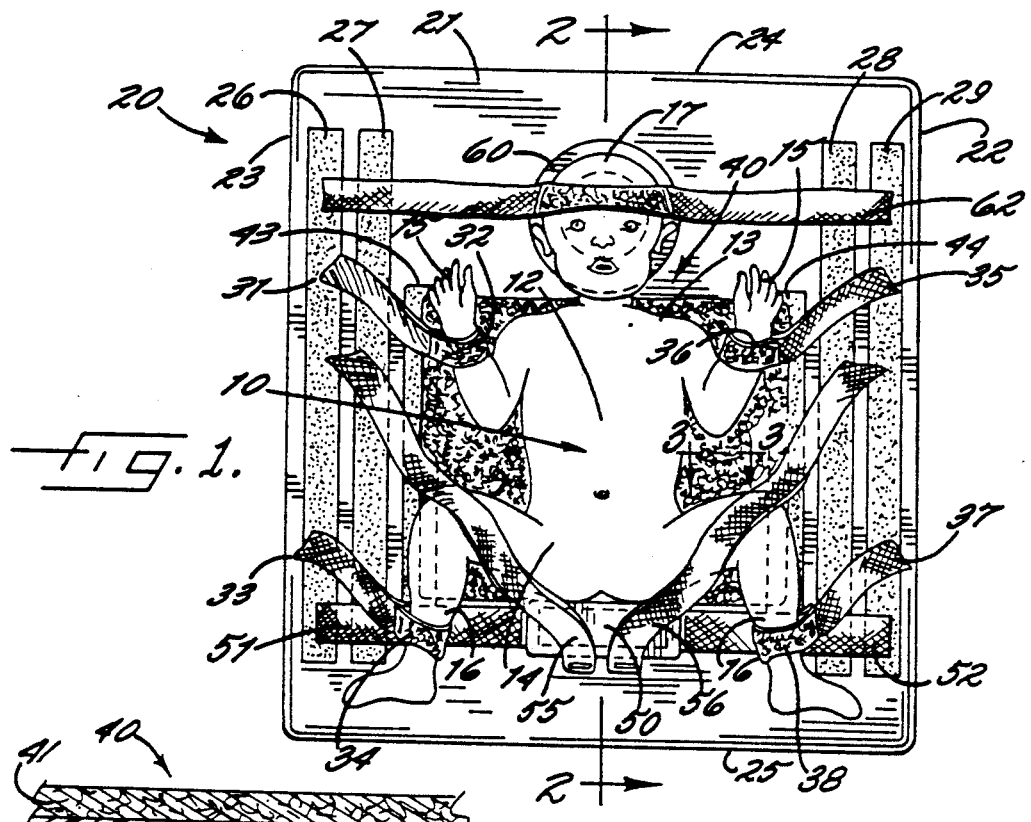

MEDICAL PATIENT RESTRAINT DEVICE

FIELD OF THE INVENTION

This invention relates to restraint devices and more particularly to a medical patient restraint device for providing additional comfort while restraining patients during surgical procedures.

BACKGROUND OF THE INVENTION

Some patients, such as infants, small children, and the elderly, characteristically resist attempts at diagnosis or treatment by physicians or by other medical personnel. Often, the combined efforts of several persons are required to restrain these patients for various medical procedures such as injections of drugs, drawing blood samples, performance of surgery requiring no or only local anesthesia, setting fractures, taking x-rays, and the like.

Medical restraint devices are generally known for restraining patients for ambulatory movement, for patient protection, for surgical procedures, and these various other medical procedures. These restraint devices for ambulatory movement and for surgical procedures typically have a support member and some type of means for securing the patient to the support member. Examples of these restraint devices may be seen in U.S. Pat. No. 4,854,305 by Bremer entitled "*Radiolucent Transport And Diagnostic Procedure Board*"; U.S. Pat. No. 4,757,811 by Clark entitled "*Infant Restraining Device*"; U.S. Pat. No. 4,108,168 by Craig entitled "*Hip Splint Device*"; U.S. Pat. No. 4,027,869 by Ruiz entitled "*Patient Restraint For X-Ray Studies Of Infants*"; U.S. Pat. No. 3,650,523 by Darby, Jr. entitled "*Infant Restraining Board*"; U.S. Pat. No. 3,526,222 by Dreibelbis entitled "*Pediatric Restraining Apparatus*"; and U.S. Pat. No. 3,215,334 by Tayman entitled "*Infant Immobilizer, Particularly For Radiological Exposure.*" These prior restraint devices, however, constrain the patient in a rigid extended manner, block easy access to the torso area of the patient, and fail to secure the patient in an appropriate position for many surgical procedures such as circumcision of an infant.

Thus, there is a need for a medical restraint device which comfortably and flexibly secures the patient in an appropriate position for surgical procedures or the like.

SUMMARY OF THE INVENTION

Therefore, the present invention provides a medical patient restraint device for additional comfort while restraining patients during surgical procedures such as the circumcision of infants. The medical patient restraint device comfortably and flexibly secures the patient in a generally spread-eagle position to provide access to the torso area of the patient during surgery or the like.

More particularly, the patient restraint device has a generally planar support member which is sized to receive and support a patient in a lying position thereon. The support member defines opposite side edges. A pair of support straps are fixed to the support member and extend along respective side edge portions in a generally parallel relationship. The pair of support straps are laterally spaced apart a distance sufficient to receive the patient therebetween with the support straps parallel to and adjacent the sides of the patient. Individual restraining straps are provided for releasable connection to respective of the patient's arms and legs. Mating fasteners are fixed to the pair of support straps and the individual restraining straps such that each of the restraining straps may be releasably attached to one of the pair of support straps so as to permit the individual restraining straps to retain the patient in a spread-eagle position on the support member and without having the individual restraining straps extending across the torso of the patient.

BRIEF DESCRIPTION OF THE DRAWINGS

Some of the objects and advantages of the present invention having been stated, others will become apparent as the description proceeds when taken in conjunction with the accompanying drawings, in which:

FIG. 1 is a top plan view of the medical patient restraint device according to the present invention and having an infant restrained thereon;

FIG. 2 is a cross-sectional view of the medical patient restraint device according to the present invention taken along line 2—2 of FIG. 1;

FIG. 3 is an enlarged fragmentary crosssectional view of the torso pad of the present invention taken along line 3—3 of FIG. 1;

FIG. 4 is an enlarged perspective view of an individual restraining strap having a ring-shaped member connected thereto;

FIG. 5 is an enlarged perspective view of the lower torso support block according to the present invention with parts broken away for clarity;

DESCRIPTION OF THE ILLUSTRATED EMBODIMENTS

Figure 6:
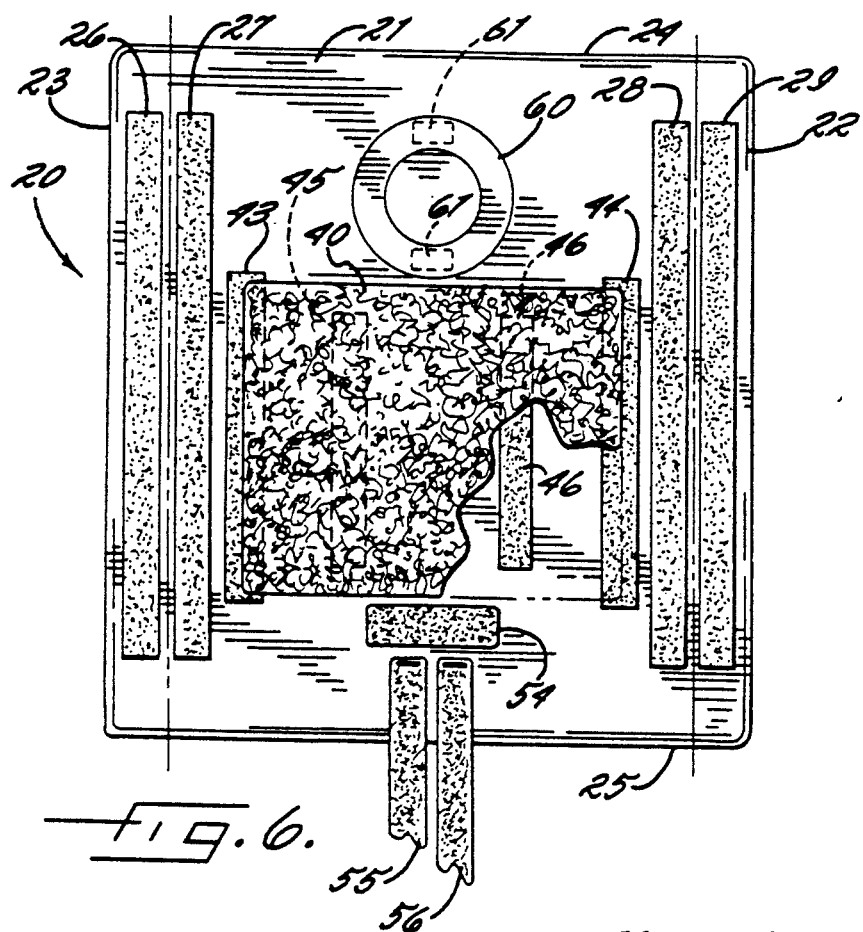
FIG. 6 is a top plan view of the medical patient restraint device according to the present invention without the infant and with parts broken away for clarity.

The present invention now will be described more fully hereinafter with reference to the accompanying drawings in which a preferred embodiment of the invention is shown. Like numbers refer to like elements throughout.

Referring now to the drawings, FIG. 1 is a top plan view of the medical patient restraint device broadly designated at 20 according to the present invention and having an infant patient broadly designated at 10 restrained thereon in a generally spread-eagle position. The medical patient restraint device 20 provides additional comfort while restraining a patient, such as the infant 10 shown, during surgical procedures such as the circumcision. The patient restraint device 20 has a support member in the form of a fabric casing 21 which is sized to receive and support a patient 10 in a lying position thereon. The fabric casing 21 has opposite side edges 22, 23 and opposite ends 24, 25 and has padded material 70 (shown in FIG. 2) disposed therein. A pair of support straps, shown as the casing straps 26, 27, 28, 29, are fixed to the fabric casing 21 and extend along respective side edge portions in a generally parallel relationship. The pair of casing straps 26, 27, 28, 29 are laterally spaced apart a distance sufficient to receive the patient 10 therebetween with the casing straps 26, 27, 28, 29 being parallel to and adjacent the sides of the patient 10. The patient restraint device 20 also has a plurality of individual restraining straps 31, 33, 35, 37 for releasable connection to respective ones of the patient's arms 15 and legs 16. The restraining straps have ring-shaped members 32, 34, 36, 38 connected thereto which extend around the patient's arms or legs as illustrated.

The patient restraint device 20 further has a pair of leg straps 55, 56 with each leg strap 55, 56 having one end thereof secured to the fabric casing 21 at a location between the pair of casing straps 26, 27, 28, 29 and adjacent one of the ends of the fabric casing 21 and such that the leg straps 26, 27, 28, 29 assume a V-shaped arrangement. This particular V-shaped arrangement provides positioning for the lower torso of the patient and enables the leg straps 55, 56 to extend around the patient's leg, preferably in the thigh region of the leg.

A head support means shown as a circular head cushion 60 attaches to the fabric casing 21 for supporting the patient's head 17 when lying on the fabric casing 21. The circular head cushion 60 preferably has a general donut configuration to provide neck support as well as head support for the patient 10 as further illustrated in FIG. 2. Also, a head strap 62 attaches to the pair of casing straps 26, 27, 28, 29 for securing the patient's head 17 to the fabric casing 21, preferably while the head and neck are supported by the circular head cushion 60.

A lower torso support block 50 attaches to the fabric casing 21 for supporting the patient's lower torso 14 when the patient 10 is positioned on the fabric casing 21. The support block 50 has a substantially rectangular shape and provides a padded stop for the patient as the patient is positioned on the fabric casing 21 for the surgical procedure or the like.

Mating fastening means shown in the form of Velcro-type fasteners are fixed to the pair of casing straps 26, 27, 28, 29, on an upper surface thereof the plurality of restraining straps 31, 33, 35, 37, the leg straps 55, 56 and the head strap 62 on a lower surface thereof such that each of the plurality of restraining straps 31, 33, 35, 37, the leg straps 55, 56, and the head strap 62 may be releasably attached to one of the pair of casing straps 26, 27, 28, 29. The Velcro-type fasteners having hooks and loops also permit the plurality of restraining straps 31, 33, 35, 37, the leg straps 55, 56, and head strap 62 to retain the patient 10 in a spread-eagle position on the fabric casing 21 and without having the plurality of restraining straps 31, 33, 35, 37, the leg straps 55, 56 or head strap 62 extend across the torso 12 of the patient 10. Also, the present invention provides a patient restraint wherein either any of the individual restraining straps 31, 33, 35, 37, either of the leg straps 55, 56, or the head strap 62 can be used individually without some of the straps or in combination for various needs of the physician or medical personnel. Further, the Velcro-type mating fasteners provide securing of the patient's arms and legs, and along with the casing straps 26, 27, 28, 29, also provide flexible attachment in various positions of the patient's body. For example, an infant generally is most comfortable with his arms folded close to the body or torso as illustrated in FIG. 1 so that securing an infant's arms in an extended or outstretched position causes discomfort and struggling movement during a surgical procedure such as circumcision. The present invention provides comfortable and flexible attachment of the restraining straps 31, 33, 35, 37 to restrain the infant in the natural folded arm position as shown instead of an extended arm or leg position. Also, the invention provides for ready attachment or detachment of the various straps described as needed by the physician during particular medical circumstances, i.e., when the patient is choking during the operation.

FIGS. 2-5 further illustrate the construction of the medical patient restraint device 20. FIG. 2 is a cross-sectional view of the medical patient restraint device 20 according to the present invention taken along line 2—2 of FIG. 1. This view illustrates the attachment of the circular head cushion 60, the torso pad 40, and the lower torso support block 50 to the fabric casing 21. Also, the padded material in the form of the support cushion 70 can be seen in this cross-sectional view. The fabric casing 21 may have an open end so that the same support cushion 70, such as the cushion found in a wheelchair as used in many hospitals and medical clinics, may be used for each restraint device 20 used. The restraint device 20 may then be disposable or thrown away after a particular surgical procedure and the same support cushion 70 used as the padded material.

FIG. 3 is an enlarged fragmentary crosssectional view of the torso pad 40 taken along line 3—3 of FIG. 1. The top layer 41 of the torso pad 40 is formed of a soft piled fabric, such as cotton or a soft synthetic yarn, for contact with the patient's skin if needed and the underside layer 42 of the torso pad 40 is formed of a woven synthetic material for attaching the torso pad 40 to the fabric casing 21. The woven synthetic layer 42 engages the pad attachment straps 43, 44, 45, 46, as further illustrated in FIG. 6.

FIG. 4 is an enlarged perspective view of an individual restraining strap 31 having a ring-shaped member 32 connected thereto. This view is also typical of the other restraining straps 33, 35, 37 shown in FIG. 1. The ring-shaped member 32 extends around the patient's arm 15 or leg 16. The ring-shaped members 32, 34, 36, 38 preferably are formed of a stretchable fabric such as terry cloth for adapting to various sized arms and legs of the patient. The stretchable fabric also provides some give in the restraining straps 31, 33, 35, 37. One side of each of the restraining straps 31, 33, 35, 37 as illustrated in FIG. 4 has either the respective mating hooks or loops of the Velcro-type fasteners. The positional location of the respective hooks or loops depends on the corresponding mating arrangement of the support straps 26, 27, 28, 29.

FIG. 5 is an enlarged perspective view of the lower torso support block 50 according to the present invention with parts broken away for clarity. The lower torso support block 50 has a substantially rectangular shape and has a pair of block straps 51, 52 for connecting the support block 50 to the fabric casing 21 along the casing straps 26, 27, 28, 29. The support block 50 preferably is formed of a lightweight padded material to also provide a more comfortable lower torso support when attached to the fabric casing 21. The support block 50 also has a Velcro-type fastener connected to an underside thereof for attaching the support block 50 to the fabric casing 21 to a corresponding mating Velcro-type fastener 54 fixed to the fabric casing 21 further illustrated in FIGS. 6 and 7. The medical personnel using the restraint device 20 may choose to use or not use the support block 50 depending on the particular procedure and need for the support block 50. The support block 50, for example, may be useful in a surgical procedure such as circumcision of an infant to comfortably support the lower torso when the physician operates.

Figure 7:
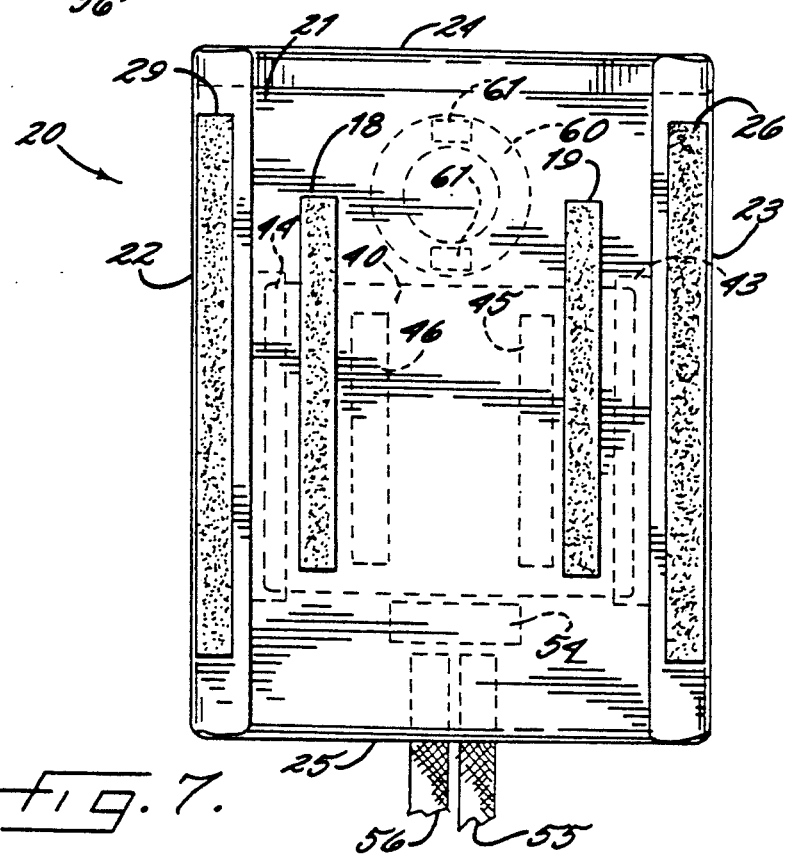
FIG. 7 is a bottom plan view of the medical restraint device according to the present invention with parts broken away for clarity.

FIGS. 6 and 7 further illustrate the attachment of the leg straps 55, 56, the torso pad 40, the circular head cushion 60, and the lower torso support block 50 to the fabric casing 21. FIG. 6 is a top plan view of the medical patient restraint device 20 according to the present invention without the infant 10 and with parts broken away for clarity. The part of the torso pad 40 broken away in this view illustrates the attachment of the torso pad 40 to the fabric casing 21 along pad attachment straps 43, 44, 45, 46. The underside of the circular head cushion 60 has the mating Velcro-type fasteners previously discussed which attach to the corresponding mating fasteners 61 fixed to the fabric casing 21. Also, the lower torso support block attaches to the corresponding mating velcro-type fastener 54 fixed to the fabric casing 21 as shown.

FIG. 7 is a bottom plan view of the medical patient restraint device 20 according to the present invention with parts broken away for clarity. This view shows a pair of casing attachment straps 18, 19 fixed to the underside of the fabric casing 21 to provide frictional resistance when the fabric casing 21 is mounted on a table or the like. This view also, when taken in conjunction with FIG. 6, illustrates the position of the casing straps 26, 29 on the underside of the fabric casing 21 so that the restraining straps 31, 33, 35, 37 may extend around and engage the casing straps 26, 29 on the underside of the fabric casing 21.

In the drawings and specification, there has been disclosed a typical preferred embodiment of the invention and, although specific terms are employed, they are used in a generic and descriptive sense only and not for the purposes of limitation, the scope of the invention being set forth in the following claims.

That which is claimed is:

1. A medical patient restraint device for providing additional patient comfort while restraining the patient during a surgical procedure such as the circumcision of an infant, said restraint device comprising:
 a generally rectangular shaped body support member sized to receive and support a patient in a reclined position thereon;
 a pair of strap means connected to said body support member and extending along respective side portions of said body support member, said pair of strap means being laterally spaced apart a distance sufficient to receive the patient therebetween and with each one of said pair of strap means being adjacent a respective side of the patient;
 individual securing means detachably connected to said pair of strap means for detachably securing each of the patient's arms and legs to said strap means without having said individual securing means extending across the torso of the patient;
 a head support member connected to a medial upper portion of said body support member for supporting the head of the patient when lying on said body support member between said pair of strap means;
 a lower torso support member connected to a medial lower portion of said body support member and positionally aligned with said head support member for abuttingly engaging the lower torso of the patient and preventing the patient from sliding off said body support member; and
 a pair of leg straps each having an end secured to a medial lower end portion of said body support member and alongside the lower extent of said lower torso support member and adapted to diagonally extend from said secured end thereof, over said lower torso support member, across an upper leg portion of the patient without extending across the torso of the patient and be detachably connected to said pair of strap means so that said pair of leg straps collectively form a generally V-shaped configuration over the patient and thereby restrain the patient in a spread eagle position.

2. The patient restraint device according to claim 1, wherein each of said individual securing means comprises a strap and a ring-shaped member connected to an end of said strap for extending around the patient's arm or leg and thereby flexibly securing the arm or leg to said body support member.

3. The patient restraint device according to claim 1, wherein said head support member comprises a circular cushion detachably connected to said medial upper portion of said body support member.

4. The patient restraint device according to claim 1, wherein said lower torso support member comprises a rectangular-shaped padded block detachably connected to said medial lower portion of said body support member.

5. The patient restraint device according to claim 1, further comprising a torso pad extending between said pair of strap means and overlying and connected to said body support member for providing cushioned comfort to the backside of the patient's torso when the patient is in a reclined position on said body support member.

6. The patient restraint device according to claim 1, further comprising a head strap for extending across the patient's head, said head strap detachably connected to said pair of strap means which are connected to said body support member.

7. A medical patient restraint device for providing additional patient comfort while restraining the patient during a surgical procedure such as the circumcision of an infant, said restraint device comprising:
 a generally rectangular shaped body support member sized to receive and support a patient in a reclined position thereon;
 a pair of side straps each having first fastening means positioned on an upper surface thereon for cooperating with second fastening means to thereby fasten a portion of the patient to each of said side straps, said pair of side straps each being secured to said body support member and being laterally spaced apart a distance sufficient to receive the patient therebetween, each one of said pair of side straps being adjacent a respective side of the patient and extending from the head of the patient beyond the lower torso thereof;
 a plurality of individual straps detachably connected to said pair of side straps and having said second fastening means positioned on a lower surface thereof for detachably securing each of the patient's arms and legs to said first fastening means positioned on the upper surface of said side straps and without having said plurality of individual straps extending across the torso of the patient;
 a head support member detachably connected to a medial upper portion of said body support member for supporting the head of the patient when lying on said body support member between said pair of straps;
 a lower torso support member detachably connected to a medial lower portion of said body support member for abuttingly engaging the lower torso of the patient and preventing the patient from sliding off said body support member; and a pair of leg straps each having said second fastening means positioned on a lower surface thereof and each of said pair of leg straps having an end fixedly secured to a medial lower end portion of said body support member and alongside the lower extent of said lower torso support member, said pair of leg straps adapted to diagonally extend from said secured end thereof, over said lower torso support member, across an upper leg portion of the patient without extending across the torso of the patient, and be detachably connected to said pair of side straps, said second fastening means of said pair of leg straps cooperating with said first fastening means of said pair of side straps so that said pair of leg straps collectively form a generally V-shaped configuration over the patient when connected to said pair of side straps and thereby restrain the patient in a spread eagle position.

8. The patient restraint device according to claim 7, wherein said first fastening means of said pair of side straps comprises hooks of hook and loop-type fasteners and said second fastening means of said plurality of individual straps and said pair of leg straps comprises loops of said hook and loop-type fasteners for ease of detachably securing the patient's arms and legs to said body support member.

9. The patient restraint device according to claim 7, wherein said first fastening means of said pair of side straps comprises loops of hook and loop-type fasteners and said second fastening means of said plurality of individual straps and said pair of leg straps comprises hooks of said hook and loop-type fasteners for ease of detachably securing the patient's arms and legs to said body support member.

10. The patient restraint device according to claim 7, wherein each of said plurality of individual straps have a ring-shaped member connected to said strap for extending around the patient's arm or leg and thereby flexibly securing the arm or leg to said body support member.

11. The patient restraint device according to claim 7, wherein said head support member comprises a circular cushion detachably connected to said medial upper portion of said body support member.

12. The patient restraint device according to claim 7, wherein said lower torso support member comprises a rectangular-shaped padded block detachably connected to said medial lower portion of said body support member.

13. The patient restraint device according to claim 7, further comprising a torso pad extending between said pair of side straps and overlying and connected to said body support member for providing cushioned comfort to the backside of the patient's torso when the patient is in a reclined position on said body support member.

14. The patient restraint device according to claim 7, further comprising a head strap for extending across the patient's head, said head strap detachably connected to said pair of straps which are connected to said body support member.

* * * * *